(12) United States Patent
Malewicz

(10) Patent No.: US 7,632,296 B2
(45) Date of Patent: Dec. 15, 2009

(54) ROLLING MEMBRANE WITH HYDRAULIC RECAPTURE MEANS FOR SELF EXPANDING STENT

(75) Inventor: Andrzej Malewicz, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 194 days.

(21) Appl. No.: 11/071,644

(22) Filed: Mar. 3, 2005

(65) Prior Publication Data
US 2006/0200221 A1 Sep. 7, 2006

(51) Int. Cl.
*A61F 2/06* (2006.01)
(52) U.S. Cl. .................. 623/1.11; 623/1.12
(58) Field of Classification Search ......... 623/1.11, 623/1.12, 1.42; 606/108
See application file for complete search history.

(56) References Cited

U.S. PATENT DOCUMENTS

| | | | | |
|---|---|---|---|---|
| 4,732,152 | A | * | 3/1988 | Wallsten et al. ........... 623/1.11 |
| 4,875,480 | A | | 10/1989 | Imbert ....................... 128/343 |
| 5,445,646 | A | | 8/1995 | Euteneuer et al. ........ 606/198 |
| 5,662,703 | A | * | 9/1997 | Yurek et al. ............... 623/1.12 |
| 5,681,345 | A | | 10/1997 | Euteneuer ................. 623/1.11 |
| 5,690,644 | A | | 11/1997 | Yurek et al. ............... 606/108 |
| 5,788,707 | A | | 8/1998 | DelToro et al. .......... 623/1.11 |
| 6,039,721 | A | * | 3/2000 | Johnson et al. .......... 604/508 |
| 6,059,813 | A | * | 5/2000 | Vrba et al. ................ 606/198 |
| 6,066,155 | A | | 5/2000 | Amann et al. ............ 606/192 |
| 6,096,045 | A | | 8/2000 | DelToro et al. .......... 606/108 |
| 6,221,097 | B1 | | 4/2001 | Wang et al. ............... 623/1.11 |
| 6,331,186 | B1 | | 12/2001 | Wang et al. ............... 623/1.11 |
| 6,342,066 | B1 | | 1/2002 | Toro et al. ................ 623/1.11 |
| 6,350,277 | B1 | | 2/2002 | Kocur ....................... 623/1.11 |
| 6,443,880 | B2 | | 9/2002 | Blais et al. ................. 492/16 |

(Continued)

FOREIGN PATENT DOCUMENTS

EP 0696447 A2 8/1995

(Continued)

OTHER PUBLICATIONS

U.S. Appl. No. 09/664,268, filed Sep. 18, 2000, Scott Hanson.

(Continued)

*Primary Examiner*—Todd E Manahan
*Assistant Examiner*—Katherine M Dowe
(74) *Attorney, Agent, or Firm*—Vidas, Arrett & Steinkraus

(57) ABSTRACT

A medical device comprising a catheter having a retractable outer sheath and a rolling membrane. The catheter includes a catheter inner shaft about which a stent in a reduced diameter configuration may be disposed. A stent retaining region of the sheath is disposed about the stent to retain the stent in the reduced diameter state prior to delivery. The rolling membrane is engaged to a portion of the outer sheath at an engagement region. The rolling membrane is positioned between the catheter inner shaft and the outer sheath and prior to retraction of the sheath the rolling membrane is disposed about at least a proximal section of the stent and is rollingly retracted therefrom when the sheath is retracted to deliver the stent. The device also recaptures a stent by pressurizing a intra-catheter space, which results in the longitudinal movement of the outer sheath in a distal direction to recover and retain the stent.

30 Claims, 9 Drawing Sheets

U.S. PATENT DOCUMENTS

| | | | |
|---|---|---|---|
| 6,478,814 B2 | 11/2002 | Wang et al. | 623/1.12 |
| 6,613,075 B1 * | 9/2003 | Healy et al. | 623/1.11 |
| 6,939,370 B2 * | 9/2005 | Hartley et al. | 623/1.11 |
| 6,942,682 B2 | 9/2005 | Vrba et al. | 606/198 |
| 2003/0114879 A1 | 6/2003 | Euteneuer et al. | 606/200 |
| 2003/0176910 A1 * | 9/2003 | Vrba et al. | 623/1.11 |
| 2004/0098079 A1 * | 5/2004 | Hartley et al. | 623/1.11 |
| 2004/0143272 A1 | 7/2004 | Cully et al. | |
| 2004/0143315 A1 | 7/2004 | Bruun et al. | |
| 2004/0199239 A1 * | 10/2004 | Austin et al. | 623/1.11 |
| 2004/0220665 A1 * | 11/2004 | Hossainy et al. | 623/1.42 |
| 2005/0033402 A1 | 2/2005 | Cully et al. | |
| 2005/0038495 A1 | 2/2005 | Greenan | |
| 2005/0070997 A1 | 3/2005 | Thornton et al. | 623/1.46 |
| 2006/0030923 A1 * | 2/2006 | Gunderson | 623/1.11 |

FOREIGN PATENT DOCUMENTS

| | | |
|---|---|---|
| WO | 96/32078 | 10/1996 |
| WO | 01/78627 A1 | 10/2001 |
| WO | 02/38084 A2 | 5/2002 |

OTHER PUBLICATIONS

U.S. Appl. No. 10/920,082, filed Aug. 17, 2004, Andrzej Malewicz.

* cited by examiner

US 7,632,296 B2

ROLLING MEMBRANE WITH HYDRAULIC RECAPTURE MEANS FOR SELF EXPANDING STENT

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates to catheters and catheter assemblies for use in medical procedures. More specifically, this invention relates to a stent delivery and recapture catheter system using a hydraulically activated rolling membrane for the delivery and/or recapture of a stent in a body lumen.

2. Description of the Related Art

Percutaneous transluminal coronary angioplasty (PTCA) is a procedure which is well established for the treatment of blockages, lesions, stenosis, thrombus, etc. present in body lumens such as the coronary arteries and/or other vessels.

A widely used form of percutaneous coronary angioplasty makes use of a dilatation balloon catheter which is introduced into and advanced through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters, vascular implants, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Prior to delivery a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. Nos. 5,681,345; 5,788,707; 6,066,155; 6,096,045; 6,221,097; 6,331,186; 6,342,066; 6,350,277; 6,443,880; 6,478,814; Ser. No. 09/664,268 and U.S. patent application Ser. No. 10/920,082 entitled Stent Delivery System, filed Aug. 17, 2004.

When stents, upon release from the catheter, are not fully released by the delivery catheter for any particular reason, do not fully expand or need to be moved or removed for various reasons, they are recaptured. Various methods have been used to achieve such objectives.

The present invention provides catheter assemblies with a variety of embodiments and features which improve stent deployment and recapture characteristics.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. For example, in at least one embodiment the invention is directed to a stent delivery catheter having an inner shaft and a distal outer sheath, the distal end of which is engaged to a rolling flexible membrane, both of which work in cooperation to retain and release the stent on and from a stent retaining region of the catheter. Prior to delivery and positioning of the stent, the inner membrane overlaps the stent and is positioned between the distal outer sheath and the stent and about the inner shaft. The catheter utilizes a pull-back mechanism, which is located at the proximal end of the catheter and is in communication with the distal outer sheath, to draw the distal outer sheath proximally. Upon retraction of the distal outer sheath via the pull-back mechanism, the connected membrane, which is connected to the distal outer sheath, is drawn proximally, rolling back over itself to expose and release the stent.

In at least one embodiment, there is a proximal outer sheath about the proximal portion the inner shaft and is positioned proximal to the distal outer sheath. The proximal end of the distal outer sheath and the distal end of the proximal outer sheath overlap to form a telescoping assembly, wherein the proximal outer sheath remains fixed relative to the inner shaft, as the distal outer sheath is allowed to longitudinally slide relative to the inner shaft, at least in response to the activation of the pull-back mechanism.

In at least one embodiment, the stent delivery catheter is designed to recapture a stent or control the axial movement of the membrane in order to recover and retain a partially released stent. In this embodiment, the distal outer sheath, the membrane, the proximal outer sheath and inner shaft form a longitudinal fluid tight intra-catheter space. A fluid port is formed in the proximal portion of the catheter so as to allow pressurization of the intra-catheter space by the forced influx of fluid. A sliding seal is provided between the distal outer sheath and the proximal outer sheath to provide a fluid tight seal and to allow longitudinal movement of the distal outer sheath relative to the proximal outer sheath. When the distal outer sheath is retracted and the membrane is rolled back upon itself, exposing the stent retaining region of the inner shaft, the intra-catheter space is pressurized by introducing fluid under pressure through the pressurization port in the catheter. As pressure is built up in the intra-catheter space, the membrane is urged distally, unrolling and drawing the distal outer sheath distally with it. As the membrane rolls distally, it rolls over the stent to be recaptured, drawing it down on the stent retaining region of the inner shaft and covering the stent. The sliding seal between the distal outer sheath and the proximal outer sheath allows the distal outer sheath to move distally with the membrane, relative to the inner shaft and the proximal outer shaft.

In at least one embodiment, at least a portion of one or more of the proximal section and distal section of the membrane is coated with a lubricious substance.

In some embodiments, the membrane may be disposed about any or all portions of the stent prior to retraction. In at least one embodiment, prior to the retraction of the sheath, the membrane is disposed about approximately half the length of the stent.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
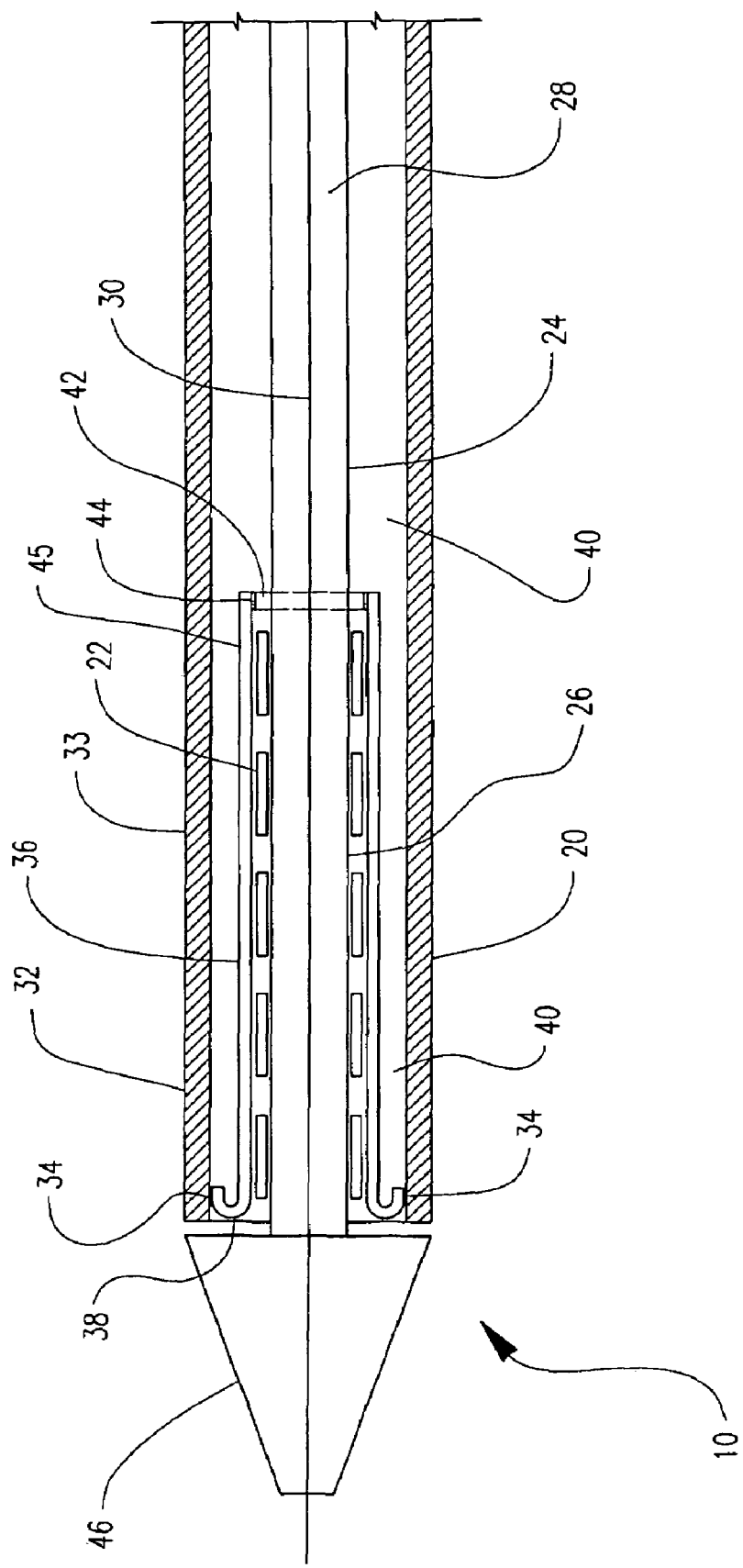
FIG. 1 is a cross-sectional side view of the distal portion of an embodiment of the invention having a rolling membrane.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
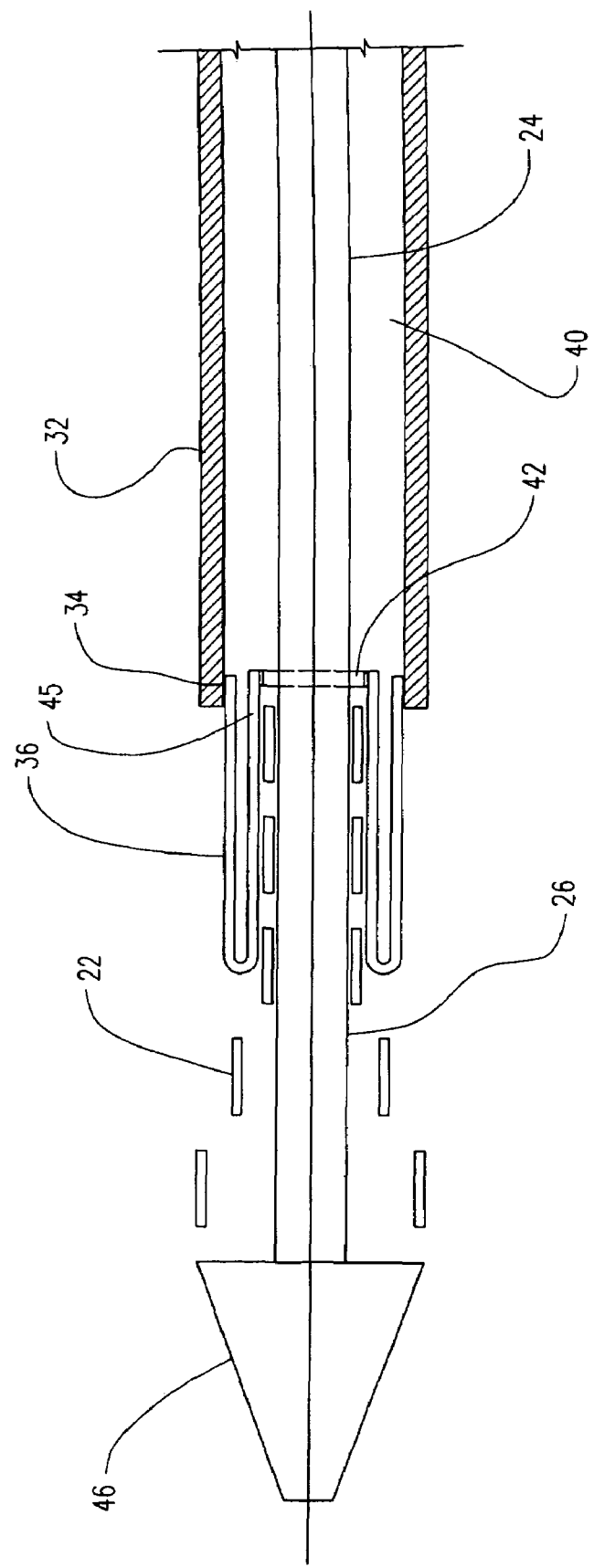
FIG. 2 is a cross-sectional side view of the embodiment depicted in FIG. 1 shown during retraction of the membrane and delivery of the stent.
Figure 3:
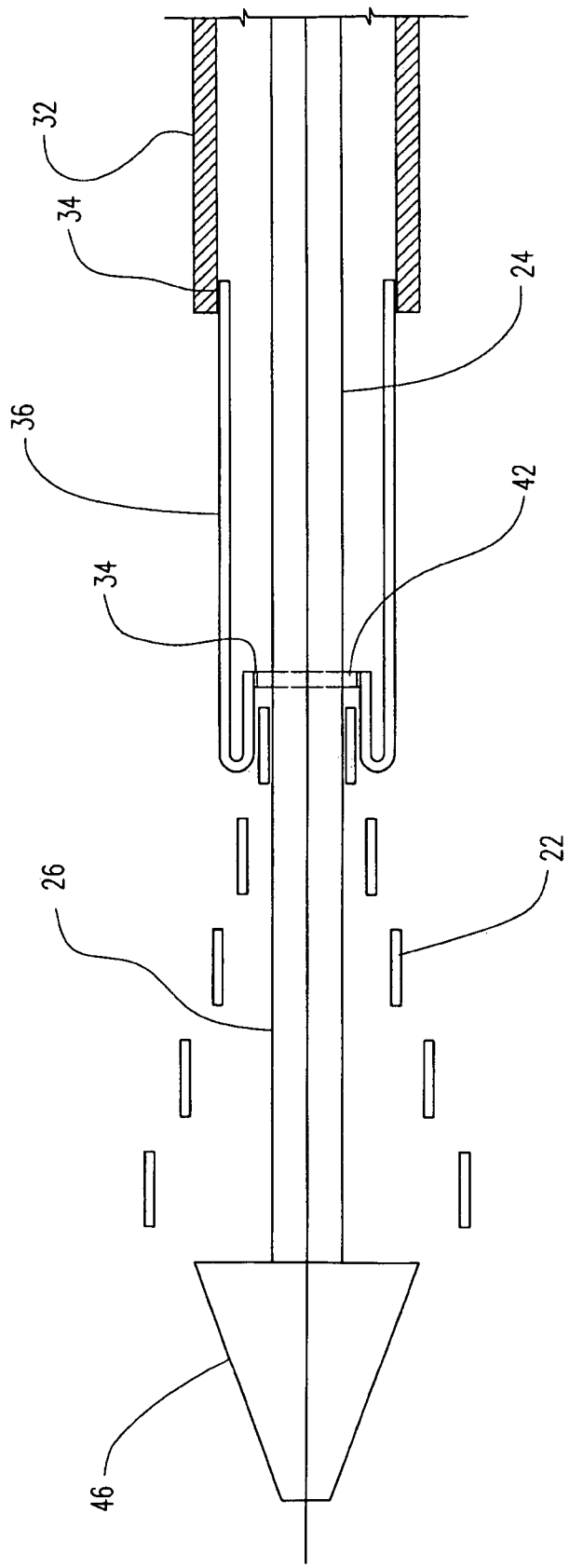
FIG. 3 is a cross-sectional side view of the embodiment depicted in FIG. 1 shown with the membrane fully retracted from the stent.

In at least one embodiment, an example of which is shown in FIGS. 1-3, the distal end of a delivery system 10 is depicted, which includes a catheter 20 which is configured to deliver a stent 22. In at least one embodiment, the stent 22 is a self-expanding stent. However, it should be understood that a medical balloon may be mounted on the catheter within the stent to be utilized to expand the stent 22.

Catheter 20 includes an inner shaft 24, a portion of which defines a stent receiving region 26. Inner shaft 24 may further define a guidewire lumen 28 through which a guidewire 30 may be passed in order to advance the catheter 20 to a predetermined position in a body lumen or vessel. Alternatively, the shaft 24 may be configured as a fixed-wire catheter.

As shown in FIG. 1, a stent 22 may be a self-expanding stent which is disposed about the stent receiving region 26 of the inner shaft 24. Self-expanding stents are well known. In some embodiments, the stent 22 may be at least partially constructed from, but not limited to, one or more of the following materials: tantalum, titanium alloys (including nitinol), and cobalt alloys, stainless steel, shape-memory polymer(s) and other materials which have elastic properties which may be used to make self-expanding stents, but may include other material or materials as well. In some embodiments the stent includes one or more areas, bands, coatings, members, etc., that is (are) detectable by imaging modalities such as X-Ray, MRI or ultrasound. In some embodiments at least a portion of the stent 22 is at least partially radiopaque.

In some embodiments the stent 22 may include one or more therapeutic and/or lubricious coatings applied thereto.

A therapeutic agent may be included with the stent. In some embodiments the agent is placed on the stent in the form of a coating. In at least one embodiment the coating includes at least one therapeutic agent and at least one polymer agent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the agent may be a polystyrene-polyisobutylene-polystyrene triblock copolymer (SIBS), polyethylene oxide, silicone rubber and/or any other suitable substrate.

In the various embodiments described herein the stent 22 is preferably configured to be at least partially self-expanding or have self-expanding characteristics. As used herein the term "self-expanding" refers to the tendency of the stent to return to a predetermined diameter when unrestrained from the catheter, such as in the manner depicted in FIGS. 1-3. In the present embodiment when the stent is disposed about the stent receiving region 26 of the inner shaft 24, the stent is restrained in its reduced diameter or pre-delivery configuration by retractable distal outer sheath 32 which is disposed about the entire length of the stent 22 prior to delivery, as shown in FIG. 1.

The distal outer sheath 32 includes a stent retaining region 33, which refers to that region of the distal outer sheath 32 which is disposed about the stent 22 prior to delivery, as seen in FIG. 1. The distal outer sheath 32 extends toward the proximal end of the catheter 20 and is configured such that it may be mechanically withdrawn proximately. Engaged to a portion 34 of the stent retaining region 33 of the distal outer sheath 32 is an inner sleeve or membrane 36. When the stent 22 is delivered, the distal outer sheath 32 and membrane 36 are retracted from about the stent in the manner illustrated in FIGS. 2-3 by pulling the distal outer sheath 32 proximally. The membrane 36 rolls back, releasing the stent.

In the various embodiments of the present invention, the rolling membrane 36 is disposed about the entire stent prior to delivery, as shown in FIG. 1. In other embodiments, the membrane 36 may be attached to the distal outer sheath 32 at a point proximal to the position indicated in the figures, but at least at a position wherein the stent is partially covered when the stent delivery system is in its delivery configuration.

In the embodiments depicted in FIGS. 1-3 the membrane 36 is a single layer membrane slightly folded over upon itself prior to delivery as shown at point 38 and bonded to the distal outer sheath 32 at point 34. When the distal outer sheath 32 is retracted, the membrane 36 is pulled back off of the stent 22 as the membrane 36 rolls proximally over itself proximally until the entire membrane 36 is rolled off of the stent 22 such as is depicted in FIGS. 1-3.

It should be understood that membrane 36 may be multi-layered and may be co-extruded.

The engagement between the distal outer sheath 32 and the membrane 36 at point 34 is a fluid-tight seal so as to prevent leakage when fluid is introduced into the intra-catheter space 40. The engagement between the distal outer sheath 32 and membrane 36 may be by welding, adhesive, physical engagement or other form of engagement. Alternatively, the engagement may be facilitated by the mutual connection to a collar, a shaped interface or other configuration.

The proximal end 45 of the membrane 36 is also engaged with the inner shaft 24 at a point proximal to the stent 22. In the embodiment shown in the figures, the membrane 36 is attached to a hub, flange, protrusion(s), marker or other member 42, which is mounted on the inner shaft 24, at point 44. Member 42 may also be provided with a diameter sufficiently greater than the diameter of the stent in the reduced state, to thereby prevent the stent from being inadvertently displaced in the proximal direction.

Alternatively, the stent 22 may be crimped directly onto the member 42. The catheter 20 may also be provided with any of the variety of stent retaining mechanisms that are known. It should be understood that the membrane 36 may be engaged directly to the inner shaft 24 as well.

The engagement between the membrane 36 and the member 42 at point 44 is also a fluid-tight seal so as to prevent leakage when fluid is introduced into the intra-catheter space 40. The engagement between the membrane 36 and the member 42 may be by welding, adhesive, physical engagement or other form of engagement. The member 42 is similarly engaged with the inner shaft 24 to form a fluid-tight seal. The member 42 may be a separate ring bonded to the inner shaft 24 or may be integrally part of the inner shaft 24.

In the various embodiments shown in and described herein the catheter 20 may employ various features to maintain the position of the stent 22 on the stent receiving region prior to deliver and/or during retraction of the sheath 36. For example a catheter tip or other member 46 may act to bias the distal edge of the stent 22 prior to delivery. The member 46 may have a diameter sufficiently greater than the diameter of the stent in the reduced state, thereby preventing the stent from being inadvertently displaced in the distal direction.

Members 42 and/or 46 may be configured to be detectable by imaging modalities such as X-Ray, MRI or ultrasound. In some embodiments at least a portion of one or both members is at least partially radiopaque.

Because the distal outer sheath 32, and particularly the stent retaining region 33 of the distal outer sheath 32, is configured to retain the stent 22 in its reduced or pre-delivery diameter, the stent retaining region 33 of the distal outer sheath 32 is constructed to have sufficient hoop strength to prevent the stent from expanding off of the stent receiving region 26 until the distal outer sheath 32 is retracted. At least the stent retaining region 33 of the distal outer sheath 32 may be constructed from one or more of the materials including, but not limited to: various formulations and combinations of polyurethane, polytetrafluoroethylene ((PTFE) including ePTFE and siliconized PTFE), polyether block amides such as PEBAX®, high density polyethylene (HDPE), polyamide, polyimide, etc. It also may be braided or be a multi-layered covered braid and may be constructed like and use materials suitable for known guide catheters.

The stent retaining region 33 of the distal outer sheath 32 is typically constructed to have greater hoop strength than the membrane 36 and therefore is less flexible than the membrane 36. The membrane 36 may be at least partially constructed of one or more of a variety of flexible materials such as including but not limited to: polyester, polyamide, polyethylene terephalate (PET), crosslinked polyethylene, polyurethane, plasticized PVC (polyvinylchloride), PTFE, nylon, polyether block amides (PEBAX), silicone, POC, polyether, etc. In at least one embodiment the membrane 36 is at least partially constructed from those materials from which medical balloons are known to be manufactured from.

It should be understood that membrane 36 may be multi-layered and may be co-extruded. In some embodiments, the membrane 36 may have an inner layer 70 and an outer layer 72 and may have a layer(s) there between, wherein the inner layer 70 partially defines the intra-catheter space 40 and the outer layer 72 covers the stent 22. Both layers 70, 72, may be made up of the materials identified for the membrane 36, as discussed above. In some embodiments, the inner layer 70 has a lower coefficient of friction than that of the outer layer 72.

During delivery of the stent 22 the sheath 32 is retracted proximally from the stent in the manner depicted in FIGS. 2-3. As a result of the engagement between the membrane 36 and the sheath 32 at the engagement region 34, during retraction the membrane 36 will roll proximally on top of itself until the entire membrane 36 is rolled off of the stent 22 as depicted in FIG. 3. To encourage the rolling action of the membrane 36, it may be coated with a lubricious. The coating may be any sort of biocompatible material such as is described in U.S. Pat. No. 5,693,034, the entire content of which is incorporated herein by reference; and/or other lubricious materials. The coating on the membrane 36 may be applied to the membranes inner surface, outer surface or both surfaces.

Figure 4:
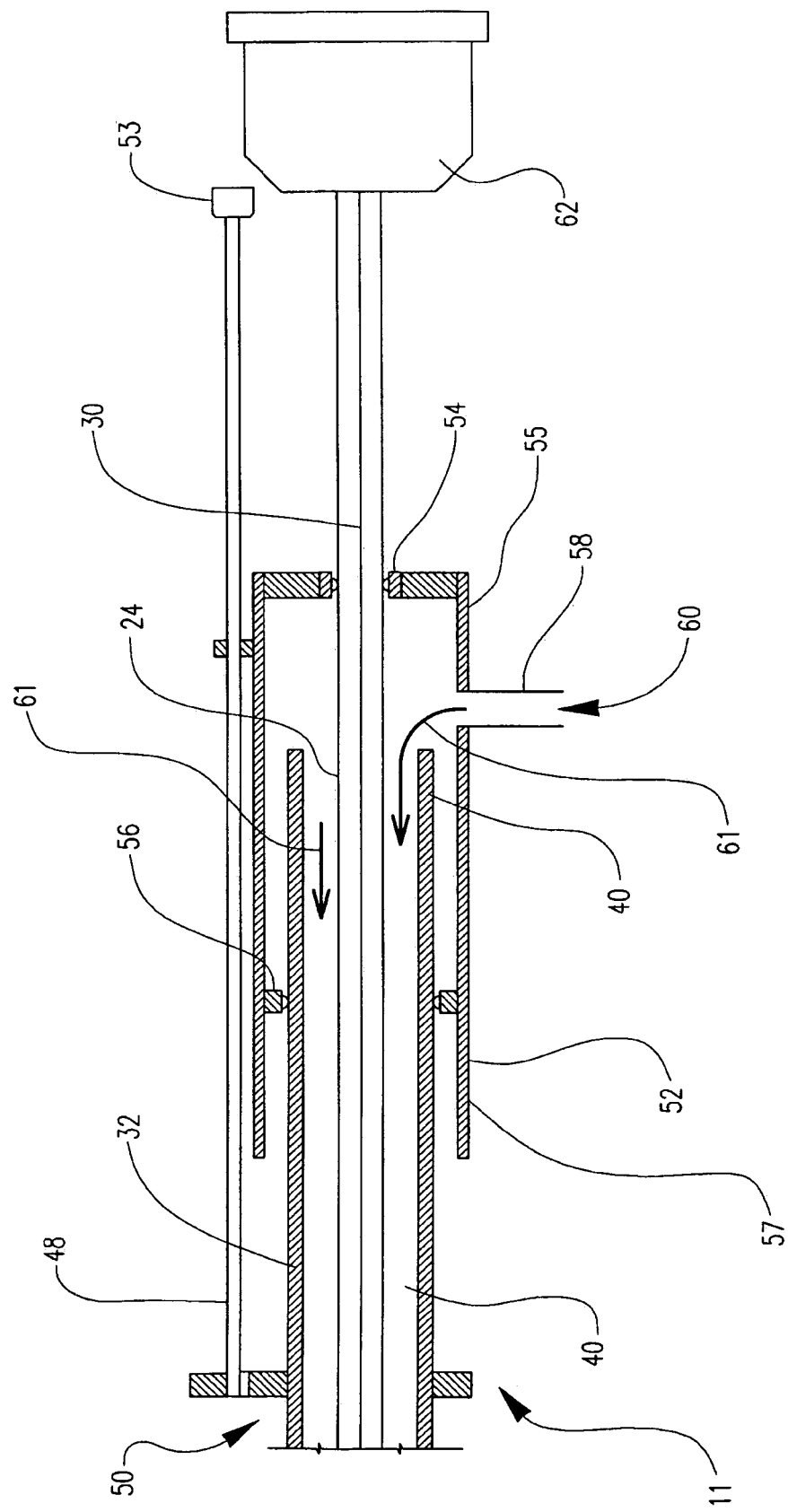
FIG. 4 is a cross-sectional side view of the proximal portion of an embodiment of the invention.

FIG. 4 shows the proximal end of the stent delivery system 10, with which the user may control the delivery and recapture of the stent 22. As can be seen, the distal outer sheath 32 extends proximally, such that it can be controlled by the user to withdraw the distal portion 33 of the distal outer sheath 32 from its position over the stent, thus releasing the stent. In this particular embodiment, a pull-back mechanism 48 is proximally positioned and is engaged with the distal outer sheath 32 at point 50. The user may retract the outer sheath by pulling on hub 53 of the pull-back mechanism 48, thus sliding the distal outer sheath 32 back relative to the inner shaft 24.

Pull-back mechanisms for retracting an outer sheath from over a stent are well known and their exact configurations may vary. What is necessary is that the user has some mechanism which they can activate, in this case by pulling, which is in physical communication with the distal outer sheath 32, which covers the stent 22 when the stent delivery catheter is in its delivery configuration, so as to withdraw the distal outer sheath 32 to release the stent 22.

In the embodiment illustrated, FIG. 4 further shows a proximal outer sheath 52. The proximal outer sheath 52 is engaged to the inner shaft 24, as shown at point 54. The engagement to the inner shaft 24 is a fluid tight seal and is similar to that of the membrane 36 to the inner shaft 24 at point 44 shown in FIG. 1. The proximal outer sheath 52 is positionally fixed relative to the inner shaft 24 at a position proximal to the distal outer sheath 32. In the embodiment shown, the proximal end 55 of the proximal outer sheath 52 is attached to the inner shaft 24.

The distal end portion 57 of the proximal outer sheath 52 overlaps with the proximal end portion 59 of the distal outer sheath 32. FIG. 4 shows the distal end portion 57 of the proximal outer sheath 52 covering the proximal end portion 59 of the distal outer sheath 32, but it should be understood that the distal end portion 57 of the proximal outer sheath 52 may be within the proximal end portion 59 of the distal outer sheath 32.

The interconnection between the sheaths 32, 52, extends the intra-catheter space 40 distally. The sheaths are interconnected via a sliding seal 56, such as a O-ring gasket made from suitable material, such as silicone. The sliding seal 56 may be affixed to either the proximal outer sheath 52 or the distal outer sheath 32 and sealing engaged with the other, such that the distal outer sheath 32 longitudinally slides relative to the proximal outer sheath 52 and the inner shaft 24. The proximal outer sheath 52 remains positionally fixed relative to the inner shaft 24. The sliding seal 56 also forms a fluid tight seal preventing leakage when fluid is introduced into the intra-catheter space 40.

In the particular embodiment shown, the proximal outer sheath 52 further has a port 58, such as a luer fitting port, through which fluid may be introduced into the intra-catheter space 40 to pressurize it. Fluid introduced flows 61 distally into the intra-catheter space 40 shown in FIGS. 1-3.

The shown embodiment further discloses a hub 62 which can be utilized in advancing the catheter and stabilizing the inner shaft 24 in the stent delivery and recapture process.

Figure 5:
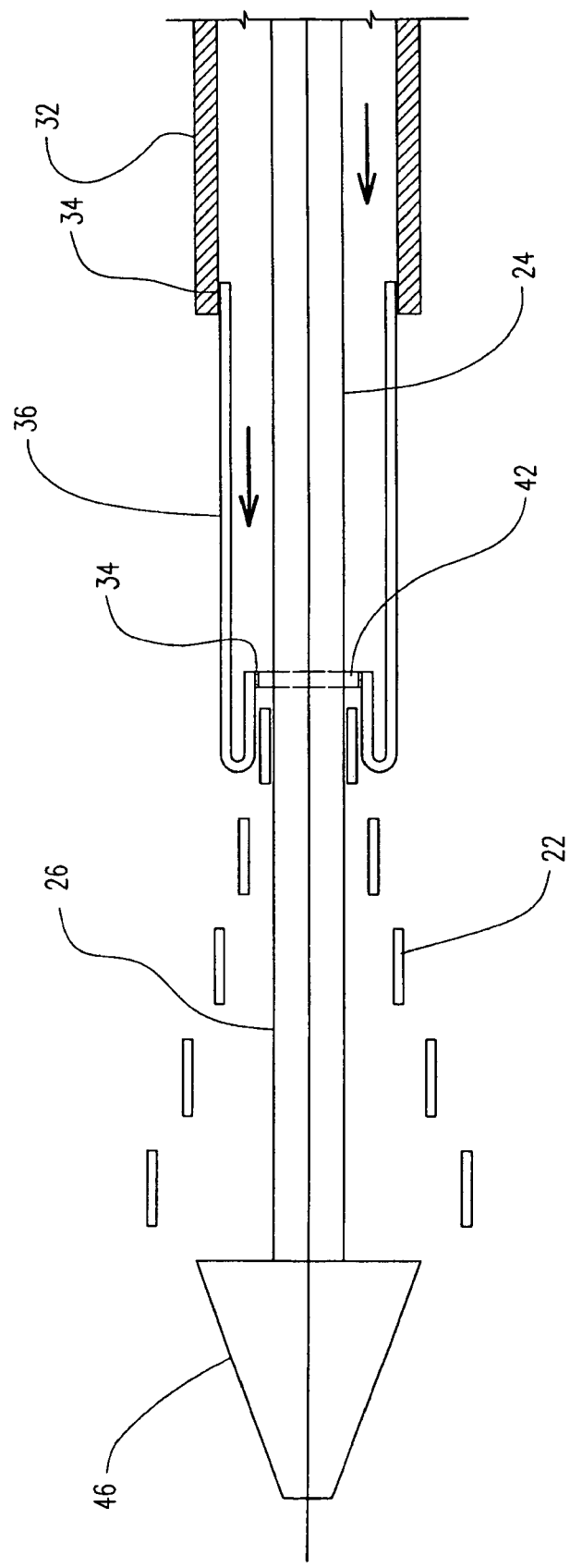
FIG. 5 is a cross-sectional side view of the distal portion of an embodiment of the invention having a rolling membrane prior to recapture of a stent.

FIGS. 4-7 illustrate the workings of the shown embodiment in the recapture of a stent which has not fully expanded or is not fully released to remove or move it. In the recapture process, the stent receiving region of the catheter is positioned within the stent 22, as shown in FIG. 5. In the case of recapturing a stent, the membrane 36 is typically not fully withdrawn from over the stent, and thus is still partially covering the stent. Once the inner shaft 24 is positioned, the intra-catheter space 40 is pressurized by the introduction of fluid through the pressurizing port 58.

Figure 6:
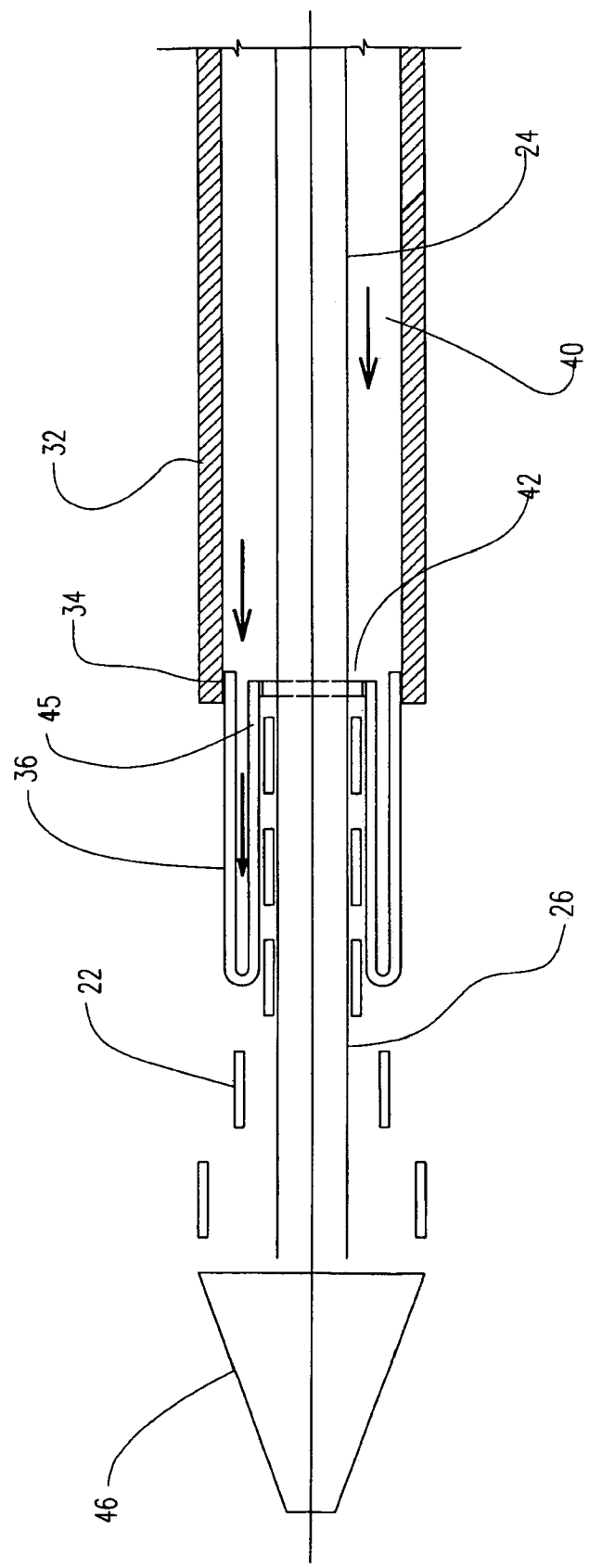
FIG. 6 is a cross-sectional side view of the embodiment depicted in FIG. 5 shown during partial recapture of the stent.
Figure 7:
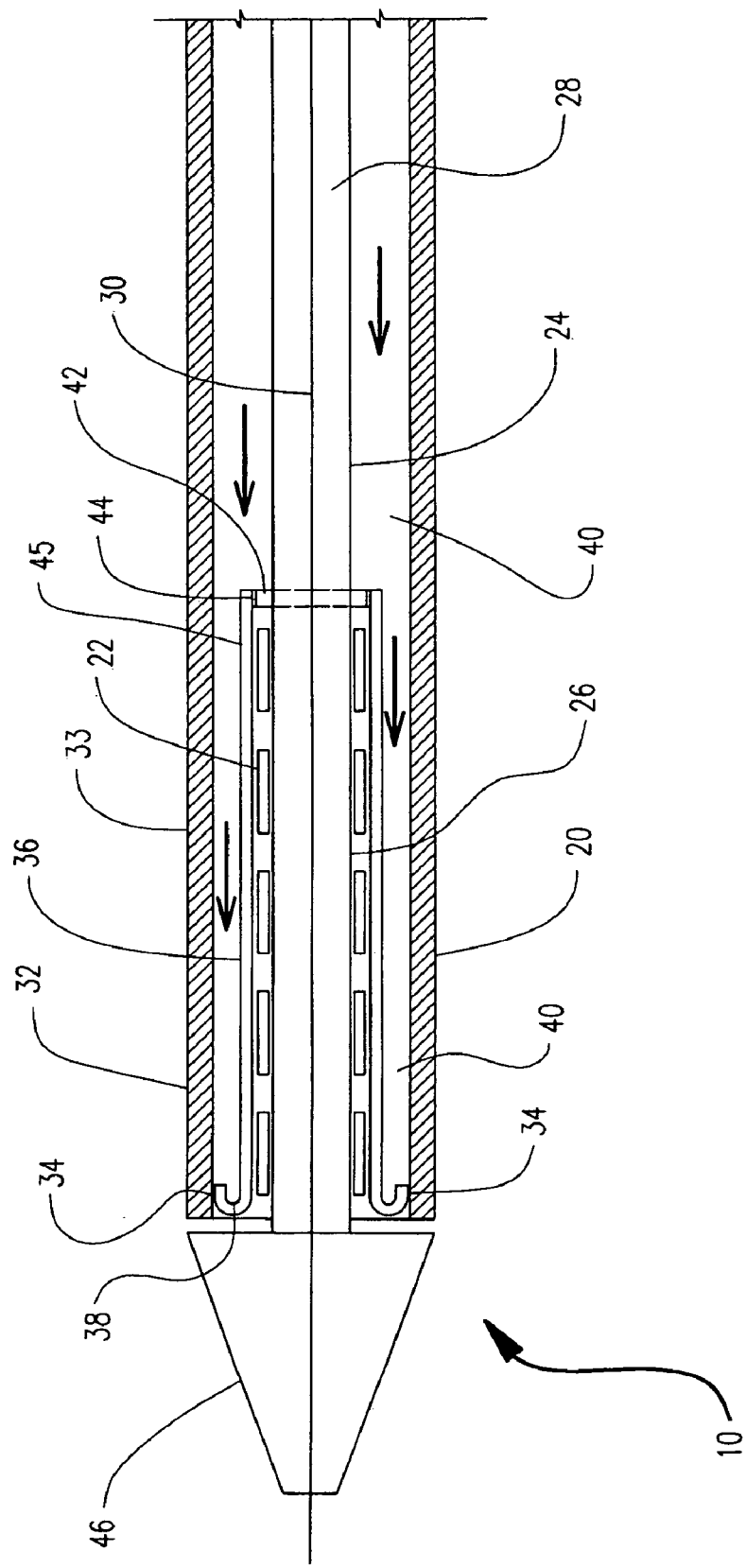
FIG. 7 is a cross-sectional side view of the embodiment depicted in FIG. 5 shown with the membrane partially covering the stent during a recapture process.
Figure 8:
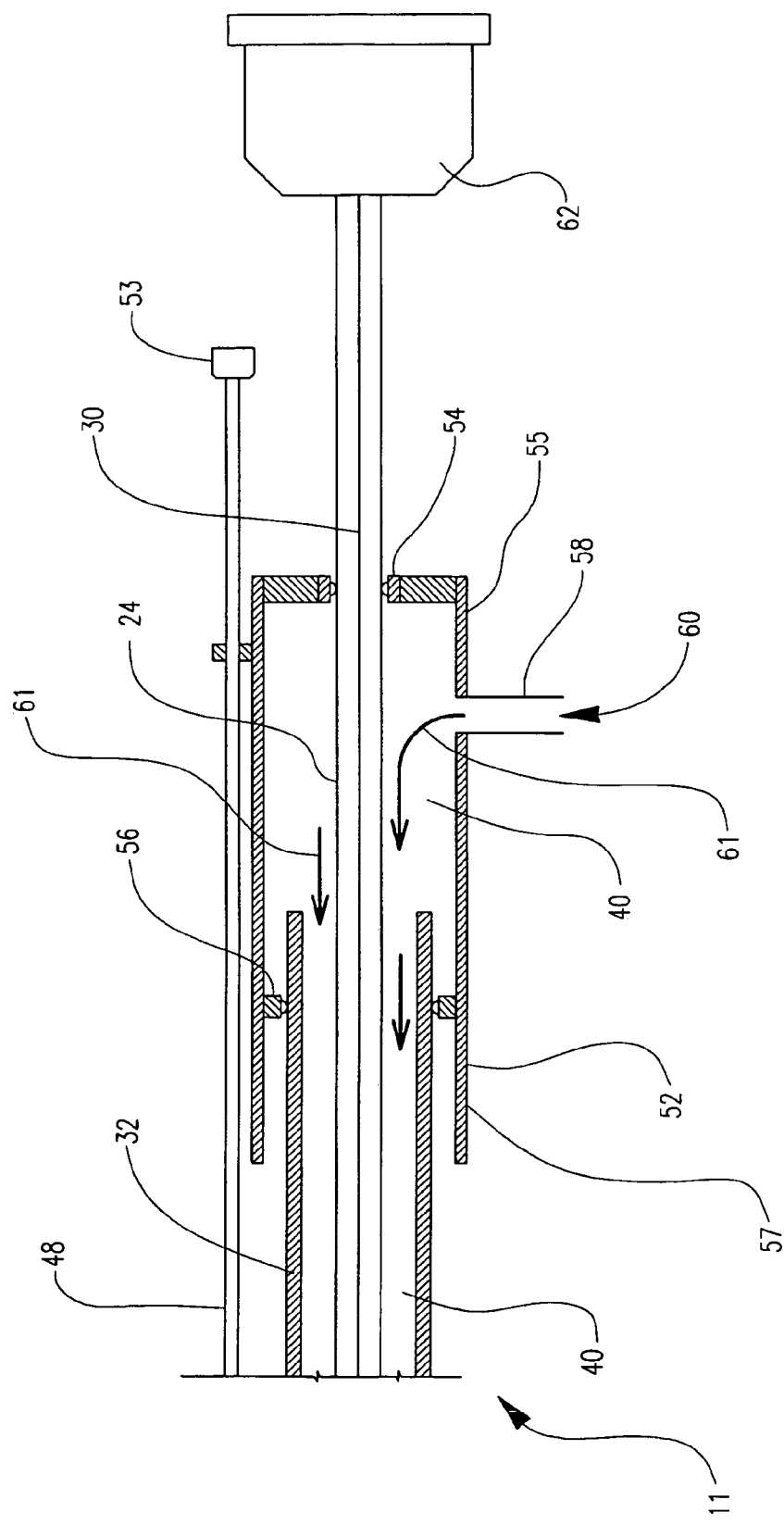
FIG. 8 is a cross-sectional side view of the proximal portion of an embodiment of the invention during the extension of the rolling membrane.
Figure 9:
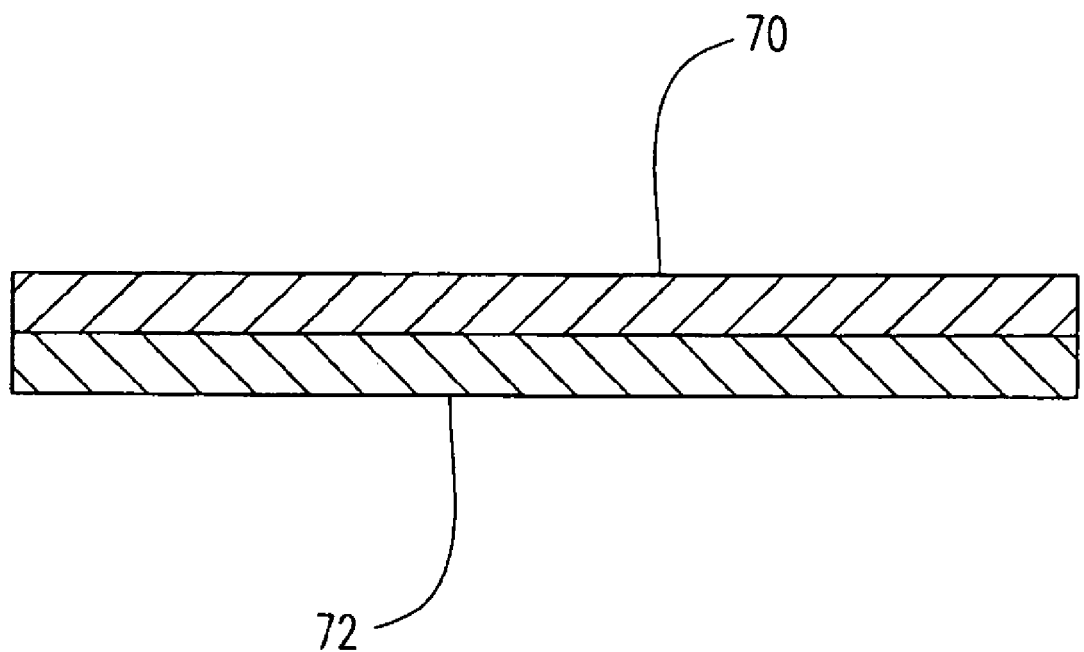
FIG. 9 is a partial cross-sectional view of a rolling membrane.

As the intra-catheter space 40 is pressurized and the inner shaft 24 is held stationary, fluid flows distally, as indicated by the arrows in FIG. 5-7. The pressurization effectively pushes the membrane 36 distally over the stent 22 to recapture it, as illustrated in FIG. 5 to FIG. 7, drawing the engaged distal outer sheath 32 with it. The distal outer sheath 32, as mentioned above, is allowed to slide distally relative to the proximal outer sheath 52 and the inner shaft 24, as illustrated in FIGS. 4 and 8. As the membrane 36 rolls distally, the stent 22 is drawn down into its contracted state and is gradually covered to a point of full containment of the stent 22, as shown in FIG. 1. After the stent is recaptured, it may be moved or removed.

The invention is further characterized by the following numbered paragraphs.

1. A method of recapturing a stent in a bodily lumen, comprising the steps of:
    providing a catheter, the having a distal portion and a proximal portion and comprising:
        an inner shaft, the inner shaft having a distal portion and a proximal portion, wherein a portion of the distal portion of the inner shaft defines a stent receiving region;
        a distal outer sheath, the distal outer sheath being about the inner shaft and being longitudinally movable relative thereto between an extended position, which is at least partially about the receiving region, and a retracted position;
        a rolling membrane having a first end and a second end, the first end being sealingly engaged with the distal outer sheath and the second end being sealingly engaged with the inner shaft; and
        an intra-catheter space, the intra-catheter space being defined by, at least in part, the rolling membrane and the distal outer sheath,
    positioning the stent receiving region within the stent,
    recapturing the stent by pressurizing the intra-catheter space, such that the rolling membrane is urged, as a result of the pressurizing, over and around the stent in a distal direction, wherein the engaged distal outer sheath resultingly is longitudinally moved toward its extended position.

2. The method of paragraph 1, a portion of the distal outer sheath defining a stent retaining region at the distal portion of the catheter, the stent retaining region being disposed about the inner shaft and being longitudinally moveable relative thereto, the retaining region being moveable between the extended position and the retracted position, which is proximal to the extended position, wherein, when the distal outer sheath is in the extended position, the retaining region is disposed about the stent receiving region and, when it is in the retracted position, the distal outer sheath is proximally removed from the stent receiving region.

3. The method of paragraph 2, wherein, when the distal outer sheath is in its extended position, the engagement between the rolling membrane and the distal outer sheath is distally positioned relative to the engagement between the rolling membrane and the inner shaft and the rolling membrane is positioned between the inner shaft and the distal outer sheath, and wherein, when the distal outer sheath is in its retracted position, the engagement between the rolling membrane and the distal outer sheath is proximally positioned relative to the engagement between the rolling membrane and the inner shaft.

4. The method of paragraph 3, further comprising a proximal outer sheath, the proximal outer sheath being disposed about the inner shaft and being longitudinally fixed relative thereto, wherein the proximal outer sheath is positioned proximal to the stent receiving region and is sealingly engaged with the distal outer sheath.

5. The method of paragraph 4, the intra-catheter space being further defined by the inner shaft and the proximal outer sheath.

6. The method of paragraph 5, further comprising a pressure port, the pressure port being in communication with the intra-catheter space, wherein, when the distal outer sheath is in its retracted position, introduction of fluid through the pressure port into the intra-catheter space causes the distal outer sheath to longitudinally move toward its extended position.

7. The method of paragraph 1, wherein, prior to recapturing the stent, the distal outer sheath is in its retracted position.

8. The method of paragraph 1, wherein, prior to recapturing the stent, the stent is at least partially within the rolling membrane.

9. The method of paragraph 6, the stent being expandable from a reduced state to an expanded state, the stent having a diameter in its reduced state that is less than the diameter in the expanded state, wherein, when the distal outer sheath is in the extended position, the stent is in the reduced state, disposed about the stent receiving region and wherein the stent has a proximal edge, a distal edge and a length measured from between the proximal edge and distal edge.

10. The method of paragraph 1, wherein, when the intra-catheter space is pressurized, the rolling membrane longitudinally rolls upon itself in a distal direction, progressively covering the stent.

11. The method of paragraph 1, wherein the stent is fully covered by the distal outer sheath as a result of the pressurizing.

12. The method of paragraph 1, wherein the rolling membrane is defined by a single layer.

13. The method of paragraph 9, wherein the second end of the rolling membrane is engaged to the inner shaft at a point proximately positioned relative to the proximal edge of the stent.

14. The method of paragraph 9, wherein the second end of the rolling membrane is sealingly attached to a raised hub on the inner shaft.

15. The method of paragraph 9, wherein the first end of the rolling membrane is sealing attached to the distal end of the stent retaining region of the distal outer sheath.

16. The method of paragraph 4, wherein a distal portion of the proximal outer sheath and a proximal of the distal outer sheath overlap and are sealing engaged with one another via a sliding seal, the sliding seal maintaining a fluid seal between the proximal outer sheath and the distal outer sheath during longitudinal movement of the distal outer sheath relative to the proximal outer sheath and the inner shaft.

17. The method of paragraph 16, wherein the proximal outer sheath is sealingly attached to a raised hub on the inner shaft.

18. The method of paragraph 1, wherein at least a portion of the rolling membrane includes a lubricious coating applied thereto.

19. The method of paragraph 18, wherein the rolling membrane has an inner surface and an outer surface, the lubricious coating being applied to at least a portion of at least one of the inner surface and outer surface of the rolling membrane.

20. The method of paragraph 1, wherein the distal outer sheath is at least partially constructed of at least one material of the group consisting of: polyurethane, polytetrafluoroethylene, high density polyethylene, polyamide, polyimide, and any combinations thereof.

21. The method of paragraph 1, wherein the rolling membrane is at least partially constructed of at least one material of the group consisting of: polyester, polyamide, polyethylene terephalate, crosslinked polyethylene, polyurethane, polyvinylchloride, polytetrafluoroethylene, nylon, polyether block amides, silicone, POC, polyether, and any combinations thereof.

22. The method of paragraph 1, wherein the catheter is a fixed-wire catheter.

23. The method of paragraph 1, wherein the inner shaft defines a guidewire lumen for passage of a guidewire therethrough.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device comprising:
  a catheter, the catheter having a distal portion and a proximal portion and comprising: an inner shaft, the inner shaft having a distal portion and a proximal portion, wherein a portion of the distal portion of the inner shaft defines a stent receiving region;
  a distal outer sheath, the distal outer sheath being about the inner shaft and being longitudinally movable relative thereto between an extended position, which is at least partially about the stent receiving region, and a retracted position, a portion of the distal outer sheath defining a stent retaining region at the distal portion of the catheter, the stent retaining region being disposed about the inner shaft and being longitudinally moveable relative thereto, the stent retaining region being moveable between the extended position and the retracted position, which is proximal to the extended position, wherein, when the distal outer sheath is in the extended position, the stent retaining region is disposed about the stent receiving region and, when it is in the retracted position, the distal outer sheath is proximally removed from the stent receiving region;
  a proximal outer sheath, the proximal outer sheath being disposed about the inner shaft and being longitudinally fixed relative thereto, wherein the proximal outer sheath is positioned proximal to the stent receiving region and is sealingly engaged with the distal outer sheath;

a rolling membrane having a first end and a second end, the first end being sealingly engaged with the distal outer sheath and the second end being sealingly engaged with the inner shaft at a point on the inner shaft proximal to the entirety of the stent receiving region, wherein the stent receiving region is between the rolling membrane and inner shaft when the distal outer sheath is in its extended position and wherein the stent retaining region of the distal outer sheath positioned radially around the rolling membrane when the distal outer sheath is in its extended position has a greater hoop strength than the rolling membrane and is less flexible than the rolling membrane; and an intra-catheter space, the intra-catheter space being defined by, at least in part, the rolling membrane and the distal outer sheath, the catheter being constructed and arranged such that the pressurization of the intra-catheter space causes the distal outer sheath to move distally relative to the inner shaft.

2. The medical device of claim 1, wherein, when the distal outer sheath is in its extended position, the engagement between the rolling membrane and the distal outer sheath is distally positioned relative to the engagement between the rolling membrane and the inner shaft and the rolling membrane is positioned between the inner shaft and the distal outer sheath, and wherein, when the distal outer sheath is in its retracted position, the engagement between the rolling membrane and the distal outer sheath is proximally positioned relative to the engagement between the rolling membrane and the inner shaft.

3. The medical device of claim 2, the intra-catheter space being further defined by the inner shaft and the proximal outer sheath.

4. The medical device of claim 3, further comprising a pressure port, the pressure port being in communication with the intra-catheter space, wherein, when the distal outer sheath is in its retracted position, introduction of fluid through the pressure port into the intra-catheter space causes the distal outer sheath to longitudinally move toward its extended position.

5. The medical device of claim 4, further comprising a stent, the stent being expandable from a reduced state to an expanded state, the stent having a diameter in its reduced state that is less than the diameter in the expanded state, wherein, when the distal outer sheath is in the extended position, the stent is in the reduced state, disposed about the stent receiving region and wherein the stent has a proximal edge, a distal edge and a length measured from between the proximal edge and distal edge.

6. The medical device of claim 5, wherein, when the distal outer sheath is in the extended position, a portion of the rolling membrane is disposed about at least a proximal section of the stent.

7. The medical device of claim 6, the at least a proximal section of the stent defining about a half of the length of the stent as measured from the proximal edge.

8. The medical device of claim 6, the at least a proximal section of the stent defining about a 50 percent to about 100 percent of the length of the stent as measured from the proximal edge.

9. The medical device of claim 5, wherein the rolling membrane is defined by a single layer.

10. The medical device of claim 9, wherein the second end of the rolling membrane is engaged to the inner shaft at a point proximately positioned relative to the proximal edge of the stent.

11. The medical device of claim 10, wherein the second end of the rolling membrane is sealingly attached to a raised hub on the inner shaft.

12. The medical device of claim 5, wherein the pressure port is located in the proximal outer sheath.

13. The medical device of claim 5, wherein the first end of the rolling membrane is sealing attached to the distal end of the stent retaining region of the distal outer sheath.

14. The medical device of claim 5, wherein a distal portion of the proximal outer sheath and a proximal portion of the distal outer sheath overlap and are sealing engaged with one another via a sliding seal, the sliding seal maintaining a fluid seal between the proximal outer sheath and the distal outer sheath during longitudinal movement of the distal outer sheath relative to the proximal outer sheath and the inner shaft.

15. The medical device of claim 14, wherein the proximal outer sheath is sealingly attached to a raised hub on the inner shaft.

16. The medical device of claim 5, wherein at least a portion of the rolling membrane includes a lubricious coating applied thereto.

17. The medical device of claim 16, wherein the rolling membrane has an inner surface and an outer surface, the lubricious coating being applied to at least a portion of at least one of the inner surface and outer surface of the rolling membrane.

18. The medical device of claim 5, further comprising a stent securing hub, the stent securing hub being engaged to the inner shaft and being positioned immediately proximal of the stent receiving region.

19. The medical device of claim 18, wherein the rolling membrane is sealingly connected to the stent securing hub.

20. The medical device of claim 19, wherein the stent securing hub is at least partially radiopaque.

21. The medical device of claim 20, wherein the stent securing hub is configured to be detectable by at least one of the following detection modalities: X-Ray, MRI, ultrasound, and any combination thereof.

22. The medical device of claim 5, wherein the distal outer sheath is at least partially constructed of at least one material of the group consisting of: polyurethane, polytetrafluoroethylene, high density polyethylene, polyamide, polyimide, and any combinations thereof.

23. The medical device of claim 5, wherein the rolling membrane is at least partially constructed of at least one material of the group consisting of: polyester, polyamide, polyethylene terephalate, crosslinked polyethylene, polyurethane, polyvinylchloride, polytetrafluoroethylene, nylon, polyether block amides, silicone, POC, polyether, and any combinations thereof.

24. The medical device of claim 5, wherein the stent is configured to be detectable by at least one of the following detection modalities: X-Ray, MRI, ultrasound, and any combination thereof.

25. The medical device of claim 5, wherein at least a portion of the stent comprises at least one therapeutic agent.

26. The medical device of claim 1, wherein the catheter is a fixed-wire catheter.

27. The medical device of claim 1, wherein the inner shaft defines a guidewire lumen for passage of a guidewire therethrough.

28. The medical device of claim 1, wherein the distal outer sheath is welded to the rolling membrane.

29. The medical device of claim 1, wherein the distal outer sheath is bonded to the rolling membrane with an adhesive.

30. The medical device of claim 1, further comprising a fluid chamber, the fluid chamber having a proximal region and a distal region, the proximal region being defined by the catheter shaft and the proximal outer sheath, the distal region being defined by the membrane and the distal outer sheath.

* * * * *

UNITED STATES PATENT AND TRADEMARK OFFICE
CERTIFICATE OF CORRECTION

PATENT NO. : 7,632,296 B2 Page 1 of 1
APPLICATION NO. : 11/071644
DATED : December 15, 2009
INVENTOR(S) : Andrzej Malewicz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 292 days.

Signed and Sealed this

Second Day of November, 2010

David J. Kappos
*Director of the United States Patent and Trademark Office*